(12) United States Patent
Lemberg

(10) Patent No.: US 6,193,710 B1
(45) Date of Patent: Feb. 27, 2001

(54) METHOD FOR SCANNING NON-OVERLAPPING PATTERNS OF LASER ENERGY WITH DIFFRACTIVE OPTICS

(75) Inventor: Vladimir Lemberg, Belmont, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

(21) Appl. No.: 09/116,648

(22) Filed: Jul. 16, 1998

(51) Int. Cl.[7] .................................................. A61B 17/22
(52) U.S. Cl. ................................... 606/5; 606/10; 606/17
(58) Field of Search ............................... 606/3–6, 10–13, 606/17, 18

(56) References Cited

U.S. PATENT DOCUMENTS

| | | | |
|---|---|---|---|
| 5,391,165 | 2/1995 | Fountain et al. | 606/4 |
| 5,546,214 | 8/1996 | Black et al. | 359/203 |
| 5,571,107 | 11/1996 | Shaibani et al. | 606/4 |
| 5,613,965 | 3/1997 | Muller | 606/5 |
| 5,646,791 | 7/1997 | Glockler | 359/831 |
| 5,683,379 | 11/1997 | Hohla . | |
| 5,782,822 | * 7/1998 | Telfair et al. | 606/5 |
| 5,891,132 | * 4/1999 | Hohla | 606/10 |
| 5,895,384 | * 4/1999 | Steiner et al. | 606/5 |

OTHER PUBLICATIONS

John K. Shimmick et al., "Axial and Transverse Displacement Tolerances During Exicmer Laser Surgery for Myopia", SPIE vol. 1423, Ophthalmic Technologies (1991), pp. 140–153.

* cited by examiner

Primary Examiner—Linda C. M. Dvorak
Assistant Examiner—Bryan K. Yarnell
(74) Attorney, Agent, or Firm—Townsend Townsend and Crew LLP; Mark D. Barrish, Esq.

(57) ABSTRACT

A method for laser treatment of the eye using one or more diffractive optical elements for producing unique treatment segments within an ablation zone on the eye. The treatment segments may be annular, pie-shaped, or have other geometries or patterns selected to apply energy in a particular manner, usually in a non-overlapping manner so that energy dosages can be precisely controlled. In a first embodiment of the method, a single diffractive optical element is used and a beam expander expands or converges the beam to achieve the different treatment segments. In a second embodiment, a plurality of diffractive optical elements are used, each of which produces a single treatment segment.

19 Claims, 8 Drawing Sheets

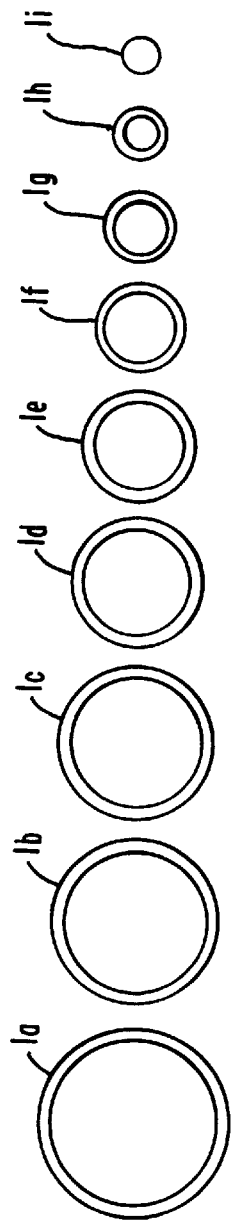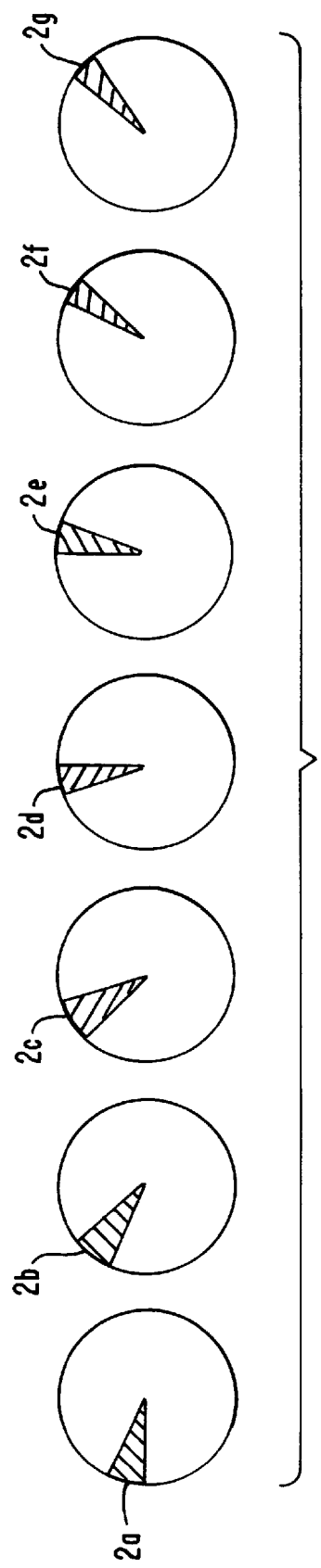
FIG. 1.
FIG. 2.

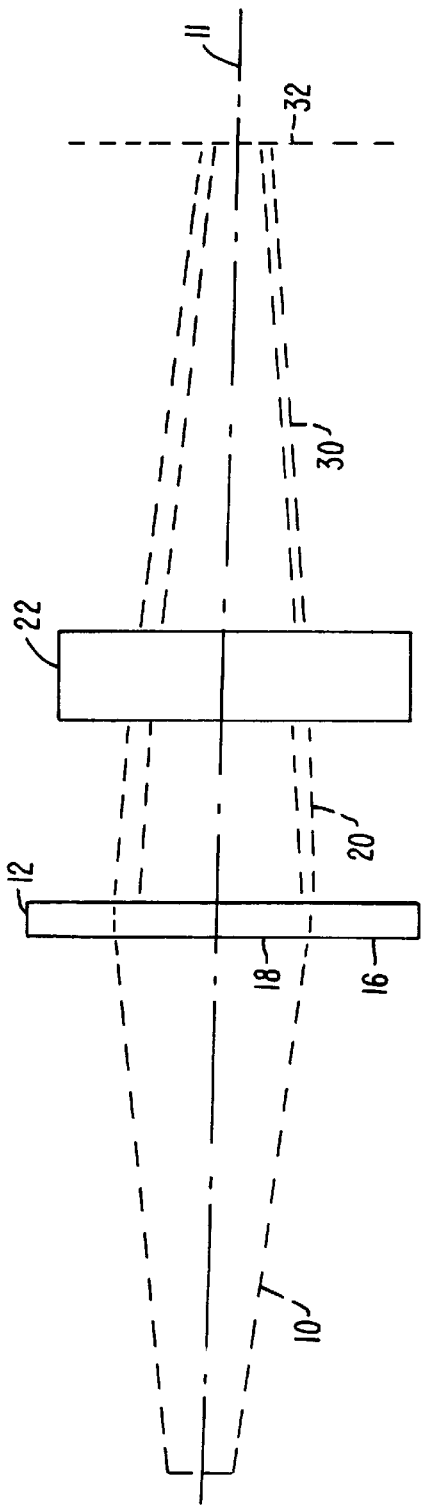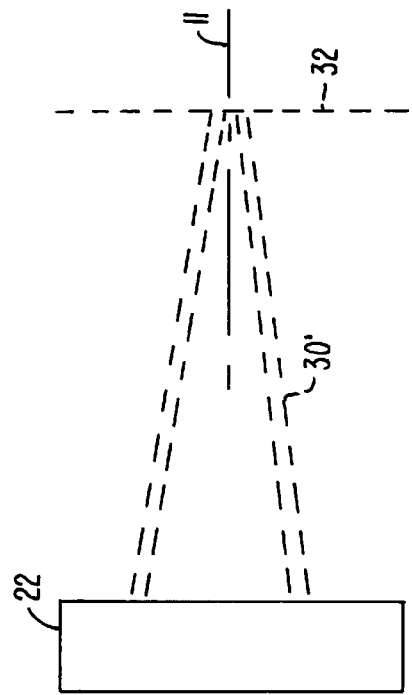
FIG. 5A.
FIG. 5B.

METHOD FOR SCANNING NON-OVERLAPPING PATTERNS OF LASER ENERGY WITH DIFFRACTIVE OPTICS

BACKGROUND OF THE INVENTION

1. Field of the Invention

The present invention relates generally to medical systems and methods. More particularly, the present invention relates to the use of diffractive optics for generating successive patterns of light energy for ablating corneal or epithelial tissue.

Photorefractive keratectomy (PRK) and phototherapeutic keratectomy (PTK) employ optical beam delivery systems for directing laser energy to a patient's eye in order to selectively ablate corneal tissue to reform the shape of the cornea and improve vision. All present commercial systems employ excimer lasers, where the beams from the lasers are spatially and temporally integrated in order to form a beam having uniform characteristics. In particular, the beams are integrated in order to display a flat intensity profile over a circular target region, often referred to as a "top hat" profile.

Once such uniformly integrated beams are achieved, they may be used in different ways in order to effect corneal ablation. In a first type of system, the beam has a width which generally corresponds to the desired target area on the cornea. The beam intensity is manipulated using an iris or other exposure control mechanism, and the desired corneal reshaping can be achieved by properly controlling the exposure. While highly effective and relatively easy to control, the need to employ a laser beam having a width equal to the treatment area (typically on the order of 5.0 mm to 10.0 mm) requires the use of large excimer lasers. Not only are such large lasers expensive, they also occupy a relatively large area, requiring significant space to house them.

As an alternative to such large beam diameter systems, laser "scanning" systems are also employed for corneal ablation. Such scanning systems employ a much smaller beam width, minimizing energy required from the laser. The smaller lasers are both more economic and require less space to house them. The use of a small beam width, however, complicates certain aspects of the treatment protocols. As most of the small treatment beams have a circular diameter, it will be appreciated that it is difficult to control exposure of the cornea. In particular, the beams overlap in non-uniform patterns as they are scanned over the cornea, making it very difficult to achieve properly controlled exposure over the entire target region. While elaborate control and exposure algorithms have been developed to minimize detrimental variations in exposure, none are entirely adequate.

For these reasons, it would be desirable to provide improved methods and systems for the scanning of light beams over corneal tissue in order to selectively ablate the tissue to treat vision disorders. In particular, it would be desirable to utilize small beam geometries with low power requirements while achieving an even energy distribution free from small regions of overexposure and underexposure. Moreover, it would be desirable to simplify the control schemes and systems required to scan small width light beams for corneal treatment. It would further be desired to provide treatment protocols and algorithms which are particularly suitable for accommodating the circular geometry of an ablation zone on the cornea. It would be still further desirable if the methods and systems could be used for the ablation of the epithelial tissue over the cornea prior to corneal treatment. At least some of these objectives will be met by the invention described hereinafter.

2. Description of the Background Art

Scanning systems for performing photorefractive keratectomy (PRK) and phototherapeutic keratectomy (PTK) are described in a number of patents, including U.S. Pat. No. 5,391,165. A laser surgical system employing a diffractive optical element adapted to an individual patient is described in U.S. Pat. No. 5,571,107. A laser scanning system employing unique reflective optics is described in U.S. Pat. No. 5,546,214. A temporal and spatial beam integrated for a PRK/PTK laser system is described in U.S. Pat. No. 5,646,791. The full disclosures of each of the above-cited U.S. patents are incorporated herein by reference.

Use of a diffractive optical element for integrating an excimer laser beam for use in PRK/PTK procedures is described in a co-pending application entitled LASER SYSTEM AND METHOD WITH DIFFRACTIVE OPTIC, U.S. patent application Ser. No. 09/015,841, filed on Jan. 29, 1998, the full disclosure of which is incorporated herein by reference.

SUMMARY OF THE INVENTION

The present invention provides improved methods, systems, and other apparatus for performing scanning-type laser ablation.

The invention is particularly useful for performing corneal ablation in PRK and PTK procedures but will also be useful for removing an epithelial layer prior to corneal ablation in such procedures. For convenience, the following discussion will be directed at corneal ablation, but the teachings are also useful for removing epithelial tissue. The use of laser energy for removing epithelial tissue is described in co-pending U.S. patent application Ser. No. 09/022,774, filed on Feb. 12, 1998, the full disclosure of which is incorporated herein by reference.

By "scanning," it is mean that an ablation light beam is aimed or "scanned" to successive, discrete locations on the corneal surface, and that those locations are then exposed to a predetermined amount or dosage of the light energy. Usually, the laser system will be operated in a pulsed manner, and the exposure at any particular location will result from a number of pulses which occur over a very short time period. The total area of the cornea to be treated, referred to hereinafter as the "ablation zone," is eventually treated as the ablative light beam scanned over the zone. As discussed above, however, prior systems which employ light beams having circular cross-sections result in an uneven treatment profile since adjacent circular geometries overlap in an uneven manner. The present invention significantly improves the uniformity of treatment, in some embodiments by employing beam geometries which are selected to cover the entire ablation zone without substantial overlap between adjacent beam patterns. In this way, the entire ablation zone can be treated with each segment or portion of the zone receiving the desired dosage of ablative energy.

The present invention provides a number of specific improvements over such prior corneal ablation methods and systems. First, the present invention provides methods and systems for treating an ablation zone with ablative light beams having annular or ring-shaped geometries. The ablation zone will usually have a circular geometry with a diameter in the range from 0.1 mm to 10.0 mm, usually from 1.0 mm to 6.0 mm. By employing successive ablative light beams having concentric, annular geometries, the entire ablation zone can be treated without substantial overlap between adjacent annular beams. That is, by utilizing adjacent annular light beams where the outer diameter of one beam is substantially equal to the inner diameter of the adjacent beam, each annular segment of the ablation zone will be treated only once. The use of annular beam geometries is particularly preferred since it facilitates dosage control over the ablation zone. That is, it will be relatively easy to expose the radially outward segments and radially inward segments to different energy dosages by properly selecting the beam intensity and dosage time of each of the radially positioned annular light beams. As described below, these annular beam geometries may also treat an ablation zone using substantial overlap between successive beams.

While the use of annular beam geometries will usually be preferred, the present invention could also utilize other beam geometries which are selected to cover individual treatment regions or segments over the total ablation zone without substantial overlap. In addition to the annular geometries described above, the treatment patterns could be pie-shaped, polygonal, irregular, or combinations thereof. In this aspect of the invention, it is important that the ablation zone be divided into a plurality of generally contiguous, non-overlapping patterns, and that each segment be treated with a discrete beam of ablative light. By then treating each of the contiguous segments with a desired dosage of the ablative light energy, total treatment of the ablation zone can be effected.

It will usually be preferably that each of the treatment segments of the ablation zone be treated only once, and that the treatment segments be non-overlapping. It would be possible, however, to devise annular, pie-shaped, or other segment geometries which are regularly and repeatedly overlapped to achieve the desired total dosage of the ablation zone in a uniform manner. For example, when employing annular treatment segments, successive treatment beams could be configured to overlap by a pre-selected distance, e.g., 50 percent of the width of the annulus. It would then be an easy matter to control the successive dosages so that each point within the ablation zone receives its desired dosage. Exposure at the boundary locations, i.e., the center region and outer peripheral annulus could be exposed with a halfwidth annulus or otherwise to achieve the desired exposure in those regions. Alternatively, the entire ablation zone can be treated with a first set of non-overlapping ablative light beams and thereafter treated with a second set of non-overlapping light beams, where the beams in the first and second set may overlap or non overlap. Thus, it can be seen that in some instances the present invention may rely on the use of successive overlapping light beams, where the beams overlap in a regular or predictable fashion which permit uniform treatment of the ablation zone to be achieved by properly controlling the energy distribution within the individual light beams.

In another aspect of the present invention, individual light beams having virtually any geometry or pattern may be provided using diffractive optics. In addition to providing the desired peripheral beam geometry, the diffractive optics may be used to provide a desired intensity profile within the individual light beam. Often, the intensity profile will be linear, i.e., will be flat or will uniformly rise or fall from the inner periphery of the light beam to the outer periphery. In other instances, the distribution may be gaussian, or may have other intensity profiles selected to achieve a desired result. Diffractive optics may be used to achieve the annular, pie-shaped, or other beam geometries described above. Often, a plurality of diffractive optical elements will be used to provide a corresponding plurality of beam geometries, where the beam geometries together cover the entire ablation zone in a non-overlapping or controlled overlapping fashion as described above. Alternatively, one or a limited number of diffractive optical elements may be utilized to establish a single beam geometry, and a beam expander used to expand or contract the beam to scan or cover the entire ablation zone. The use of a diffractive optical element together with a beam expander is particularly useful with annular beam geometries which can readily be expanded and decreased in diameter to provide successive, concentric beams to cover the entire circular ablation zone. Still further, a single limited number of diffractive optical elements can be used together with means for rotating the beam to scan the entire ablation zone. For example, when using pie-shaped beam geometries, the beam can be rotated to cover adjacent pie-shaped sections of the ablation zone in a non-overlapping or overlapping fashion. Rotation of the beam can be achieved by rotating the diffractive optical element or by providing optics downstream of the diffractive optical elements to rotate the beam in a selective fashion.

In all of the above, the ablative light energy will usually be laser energy, more usually being energy from an excimer laser, still more usually having a wavelength of about 193 nm. The beam patterns will typically have an area in the range from 0.01 mm$^2$ to 50.0 mm$^2$, more usually from 1.0 mm$^2$ to 40.0 mm$^2$. Successive beams may have the same or different areas, but each of the areas will typically be in the ranges set forth above. Each beam will typically have a power sufficient to maintain the minimum or threshold energy intensity required for corneal ablation, usually having a total energy in the range from 0.016 mJ to 80.0 mJ, usually from 1.6 mJ to 64.0 mJ. Such energy levels can conveniently be achieved with excimer lasers having a total power output in the range from 0.16 mW to 80 W, usually from 1.0 mW to 10.0 W. The methods will usually employ at least about 3 successive patterns, usually at least about 30 successive patterns, typically being in the range from 4 to 1,500 successive patterns, more typically being in the range from 6 to 300 successive patterns.

The present invention also provides systems for ablating corneal tissue over an ablation zone. The systems comprise a coherent light source which produces an ablative light beam having a beam geometry. The system further comprises a means for transforming the beam into a plurality of successive patterns, where each pattern covers a portion of the ablation zone. Usually, each of the patterns will have a unique geometry, with no two patterns being the same. By "unique geometry," it is meant that the beam will have a unique peripheral geometry, a unique orientation in space, and/or unique dimensions. Examples of such unique geometries, include annular rings having different diameters and usually different annular widths and pie-shaped patterns having different radial orientations but otherwise having similar dimensions. Usually, the different patterns will have a total area within the ranges set forth above. In the case of annular beam geometries, this will usually mean that the outermost rings will have smaller annular widths than the inner rings in order to help balance the beam intensity over the ablation zone. In some instances, of course, it may be desirable to have higher beam intensities near the center of the ablation zone when it is desired to remove more tissue in the center relative to the outer periphery. The systems will usually employ lasers or other coherent light sources having a power output in the range from 0.16 mW to 80.0 W.

A first exemplary system according to the present invention will employ a plurality of diffractive optical elements to produce the different beam patterns. In particular, each diffractive optical element will be adapted to transform the ablative light beam into one of the patterns. The system will further comprise a positioner which selectively places the diffractive optical elements in the path of the ablative light beam to transform the beam into the respective patterns. The diffractive optical elements will be adapted and selected so that the entire ablation zone can be covered by successively applying the light beams produced by the elements.

In a second exemplary system, means for transforming the ablative light beam will comprise one or a limited number of diffractive optical elements adapted to transform the ablative light beam into an annular pattern. The system will further comprise a beam expander which receives the ablative annular light beam and selectively adjusts the diameter of the annulus to produce the desired successive beam patterns.

The present invention still further comprises a programming card for use with a laser ablation system for ablating corneal tissue. The programming card comprises a tangible medium which stores computer-readable code. The code sets forth any of the methods set forth above for ablating corneal tissue.

BRIEF DESCRIPTION OF THE DRAWINGS

FIG. 1 illustrates a plurality of successive and annular beam geometries which may be utilized in the methods and systems of the present invention for treating corneal tissue.

FIG. 2 illustrates a series of successive pie-shaped beam geometries which can be utilized in the methods and systems of the present invention for treating corneal tissue.

FIGS. 5A and 5B are detailed schematic views of the apparatus of FIG. 4.

DESCRIPTION OF THE SPECIFIC EMBODIMENTS

Referring now to FIG. 1, the methods and systems of the present invention will preferably employ a plurality of annular beam geometries as illustrated in FIG. 1. Most simply, successive rings $1a$–$1i$ may be projected onto the corneal tissue, where the outer diameter of each successive beam (e.g., $1b$) is equal to the inner diameter of the previous beam (e.g., $1a$). The final beam $1i$ will then cover the entire opening from the previous beam $1h$. While it will usually be preferred to use a series of such successive, non-overlapping annular beams, it will also be possible to employ beams which overlap in a predictable manner so that the total dosage of ablative light energy to any point on the cornea can be controlled. It may also be possible to employ annular beam shapes that are elliptical, or having some other non-circular peripheral geometry.

As an alternative to the annular beam geometry shown in FIG. 1, the methods and systems of the present invention could project pie-shaped beams $2a$–$2g$, as shown in FIG. 2. A sufficient number of additional pie-shaped beams will be utilized to cover the entire circular ablation zone, where the individual pie-shaped segments may have the same or different sizes, usually being the same. Also usually, the pie-shaped segments will be successively projected in a non-overlapping manner, although it would also be possible to provide regular overlapping of the segments so long as the total dosage of any particular point on the corneal tissue is taken into account.

Figure 3:
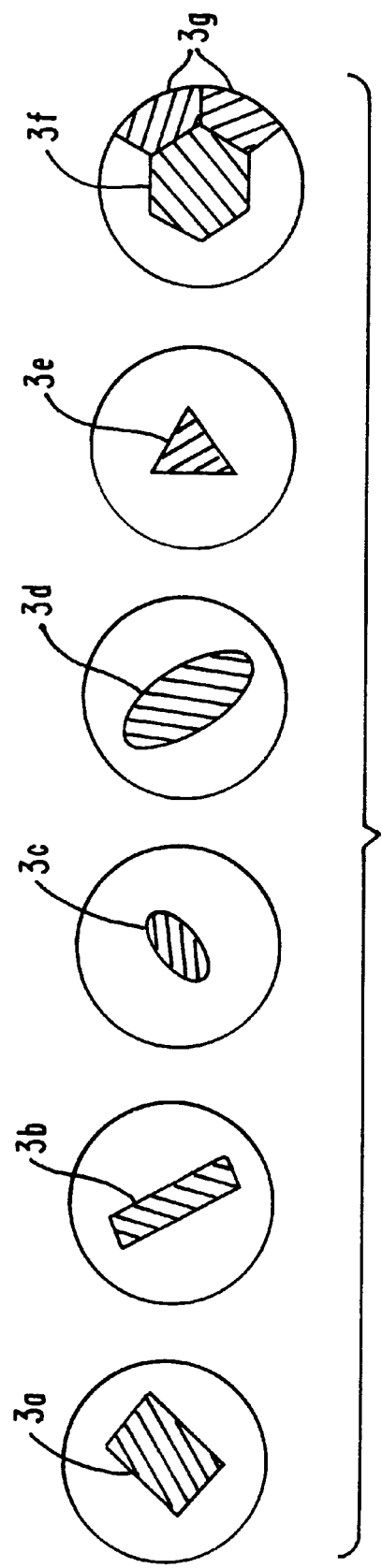
FIG. 3 illustrates a series of other beam geometries which can be utilized for treating corneal tissue in the methods and systems of the present invention.

Shown in FIGS. 1 and 2, exemplary schemes for treating an entire ablation zone are illustrated. In some instances, however, it will be desirable to treat only more limited regions within the ablation zone, as shown in FIG. 3. In particular, the treatment of astigmatism will often require treatment of one or more rectangular zones within the larger ablation zone, as shown at $3a$ and $3b$. Elliptical and polygonal treatment regions, as shown at $3f$ may also find use in particular circumstances. For example, the hexagonal pattern $3f$ may be projected to treat a central region within an ablation zone, with the peripheral regions subsequently being treated with partial pie-shaped regions $3g$. As described in more detail below, use of diffractive optical elements according to the methods and systems of the present invention will be particularly useful for producing such particular beam geometries as shown in FIG. 3.

Figure 4:
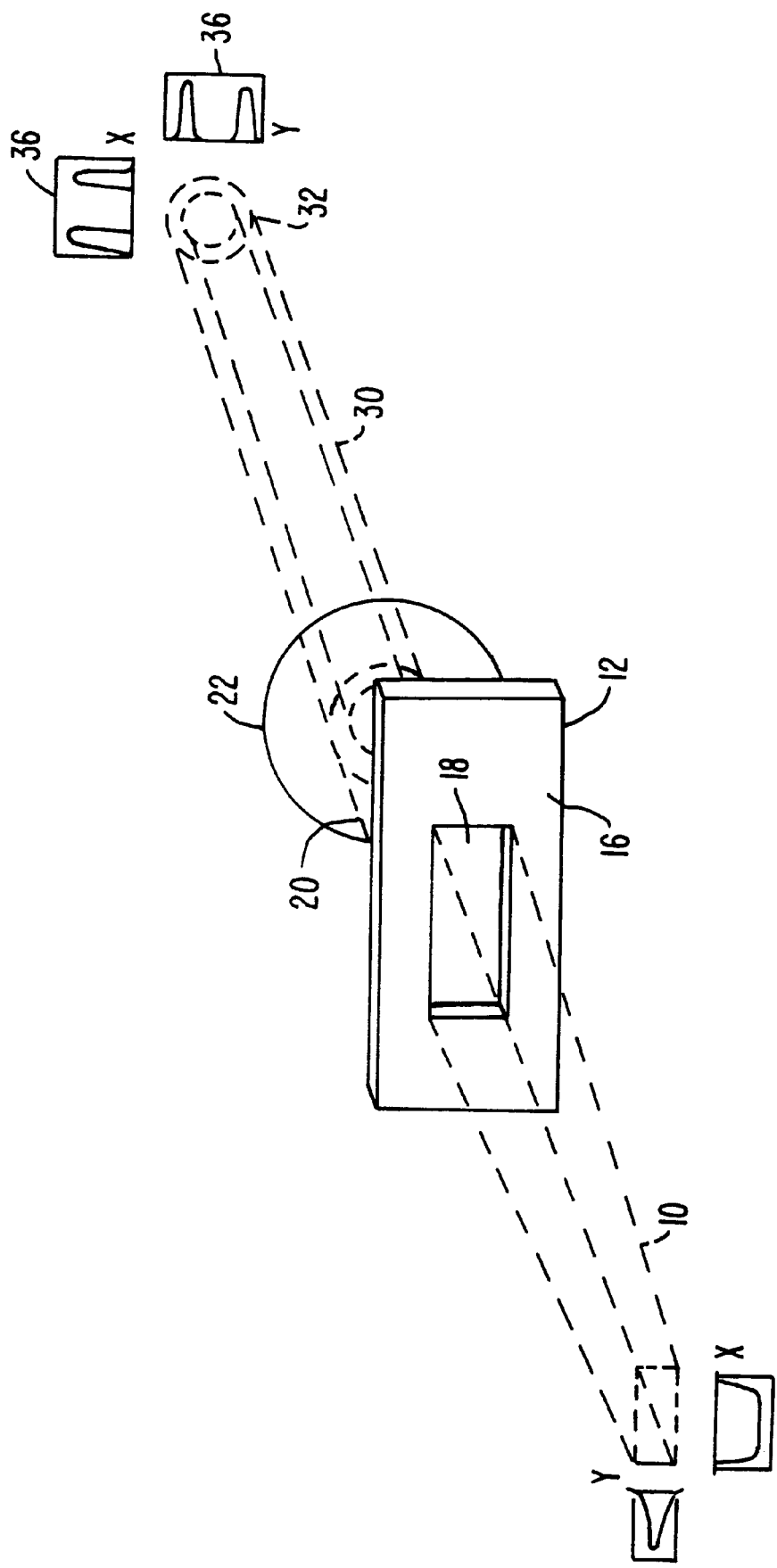
FIG. 4 is a schematic view of a diffractive optical apparatus for transforming an ablative light beam into an annular beam geometry in accordance with the present invention.

Referring now to FIGS. 4 and 5, a first diffractive optical system for producing an annular beam geometry according to the present invention will be described. A generally rectangular excimer laser beam 10 is projected along the beam axis 11 toward a diffractive element 12. The intensity along the long axis (x-axis) of the beam 10 is generally uniform, while the intensity along the short axis (y-axis) is substantially gaussian. The diffractive element 12 has a generally planar body 16 that includes a transparent portion 18 which receives and diffractively transforms the laser beam 10 into an annular geometry. The diffracted annular beam 20 emerging from the diffractive element 12 travels along the beam axis 11 through a beam expander assembly (zoom lens) 22 which expands or converges the diffracted beam 20. The annular beam 30 travels along the beam axis 11 and has a transformed pattern at a spatial plane 32 where the patient's eye will be located in the larger treatment system.

Diffractive Optic Apparatus

Referring to FIG. 4, the transparent portion 18 has a generally rectangular shape sized for receiving the entire rectangular beam 10. However, for beams which are not rectangular, transparent portion 18 may desirably be circular, square, or other appropriate shapes which match beam 10. The transparent portion 18 of the diffractive element 12 has a diffractive pattern etched in a transparent medium. The transparent medium may be a glass-like silica material. The transparent medium desirably is substantially non-absorbent and non-reflective to the excimer laser beam 10. For instance, the transparent medium may include fused silica, quartz, magnesium fluoride, calcium fluoride, lithium fluoride, or sapphire.

The diffractive pattern on the transparent medium forms a diffractive grating that is configured to transform the excimer laser beam 10 to beam 20 having an annular geometry. Usually, but not necessarily, the grating will further transform the beam 10 to have a spatial intensity distribution that is substantially uniform across the annulus of the beam.

The configuration of the diffractive grating depends largely on the shape and spatial intensity distribution of the desired annular converged beam 30, and also on the characteristics of the incoming beam 10 such as its wavelength and spatial intensity distribution. The diffractive pattern may include a plurality of properly spaced etched regions such as lines, spots, or the like. For excimer lasers with short wavelengths in the neighborhood of about 193 nm, the spacings of the etched regions in the diffractive pattern are advantageously small and precise. Known etching techniques such as dry etching may be used to etch the diffractive pattern on the transparent portion 18.

As illustrated in FIG. 4, the beam expander assembly 22 will focus as well as expand/converge the annular beam 30 onto the spatial integration plane 32. Expander assembly 22 may have a movable lens to vary a size of the beam at plane 32. The cross-section of the projected beam 30 at the spatial integration plane 32 is substantially annular and has a spatial intensity distribution 36.

In operation, the laser beam 10 is directed along the beam axis 11 through the transparent portion 18 of the diffractive element 12 which is aligned with the laser beam 10 to receive the entire laser beam 10. The etched diffractive pattern of the transparent portion 18 serves as a diffractive control angle diffuser for transforming the spatial intensity distribution of the laser beam 10 into the desired annular geometry. The transparent portion 18 may transform the generally rectangular gaussian laser beam 10 to the generally annular beam 20 with a substantially uniform intensity distribution across the width of the annulus. The beam expander assembly 22 is aligned with the beam axis 11 and converges the spatially integrated beam 20 to a desired size.

Referring now in particular to FIGS. 5A and 5B, the beam expander 22 will be a conventional optical assembly, such as a conventional zoom-lens assembly. The beam expander assembly 22 will be used to project successive annular beams 30 (FIG. 5A) and 30' (FIG. 5B) having different diameters. It will be appreciated that the beam expander can thus be utilized to produce the successive annular beam patterns as shown in FIG. 1 which are useful for treating an entire ablation zone according to the present invention.

Figure 6:
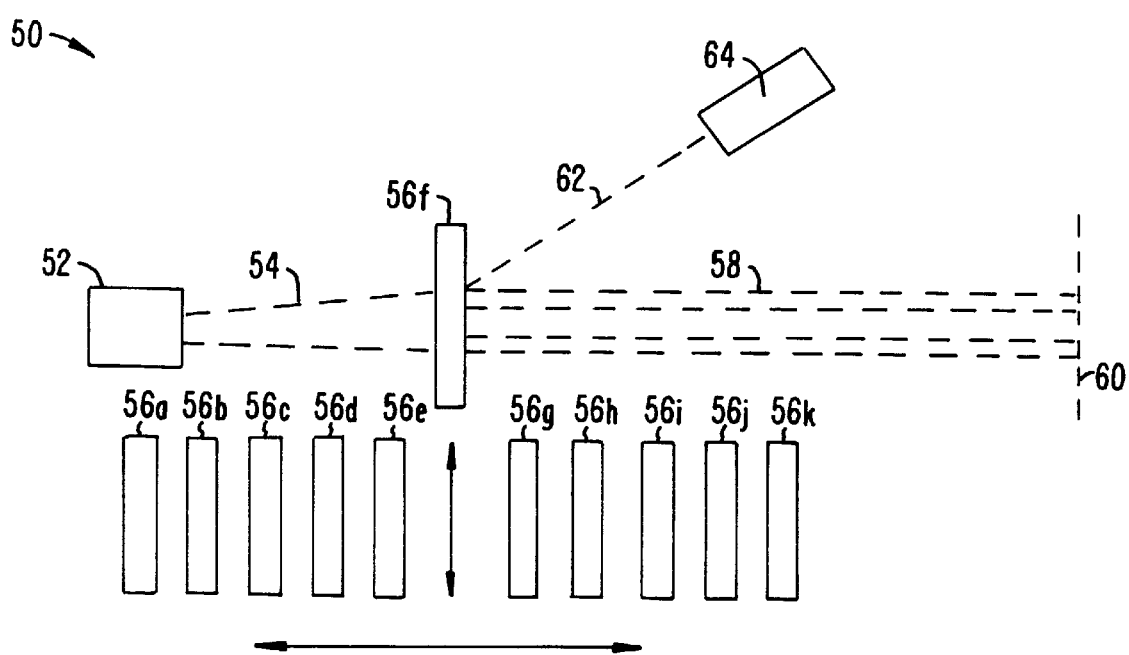
FIG. 6 is a schematic illustration of an alternative system according to the present invention for transforming ablative beam geometry according to the present invention.

Referring now to FIG. 6, an alternative system 50 for producing successive discrete beam geometries is illustrated. A laser 52 produces a beam 54 which may have any of the geometries described above, typically being a rectangular excimer laser beam. A plurality of diffractive optical elements 56a–56k are provided and may be selectively placed to receive the incident ablative light beam 54 and produce a desired projected beam 58 which is focused at the beam integration plane 60. The geometry of the projected beam 58 may be annular, pie-shaped, or any of the other geometries described above. The diffractive optical elements 56a–56k can be utilized not only to impart the basic beam geometry, but also to spatially and temporally integrate the beam as well as focus the beam at the beam integration plane 60. The system, however, can also be used together with other more conventional optics for focusing and scanning the beam at the eye of the patient, as described below in more detail with an exemplary system for the present invention. For example, the diffractive optical elements 56a–56k may be configured to a portion 62 of the beam laterally to an intensity detector 64 in order to monitor system performance. The system 50 will include mechanisms for selectively and sequentially positioning each of the diffractive optical elements 56a–56k at the desired location between the laser 52 and integration plane 60 in order to provide for proper transformation and focusing of the beam.

Figure 7:
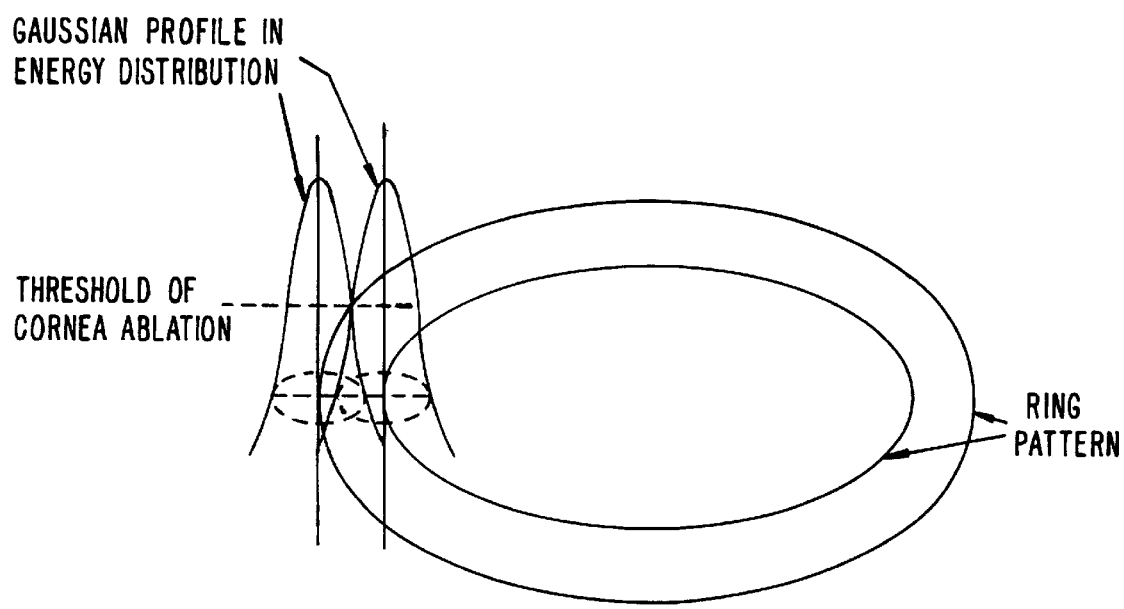
FIG. 7 illustrates a pair of successive annular ring geometries for treating corneal tissue according to the methods of the present invention.

Referring now to FIG. 7, the preferred annular beams may have linear, flat, gaussian, or other energy distributions across their annular widths. The use of annular beams having gaussian energy distributions is shown in FIG. 7. In each successive annular ring, the laser energy will intersect with the prior and subsequent beam at a point in the distribution profile where the energy is at or below the minimum threshold necessary for ablating corneal tissue, i.e., about 60 mJ/cm$^2$. In other instances, the successive annular rings will be positioned with abrupt edges so that the beams may be positioned with no space between successive beams. In alternative embodiment, the subsequent beams may intersect above the minimum ablation threshold so that the ablations overlap.

Figure 8:
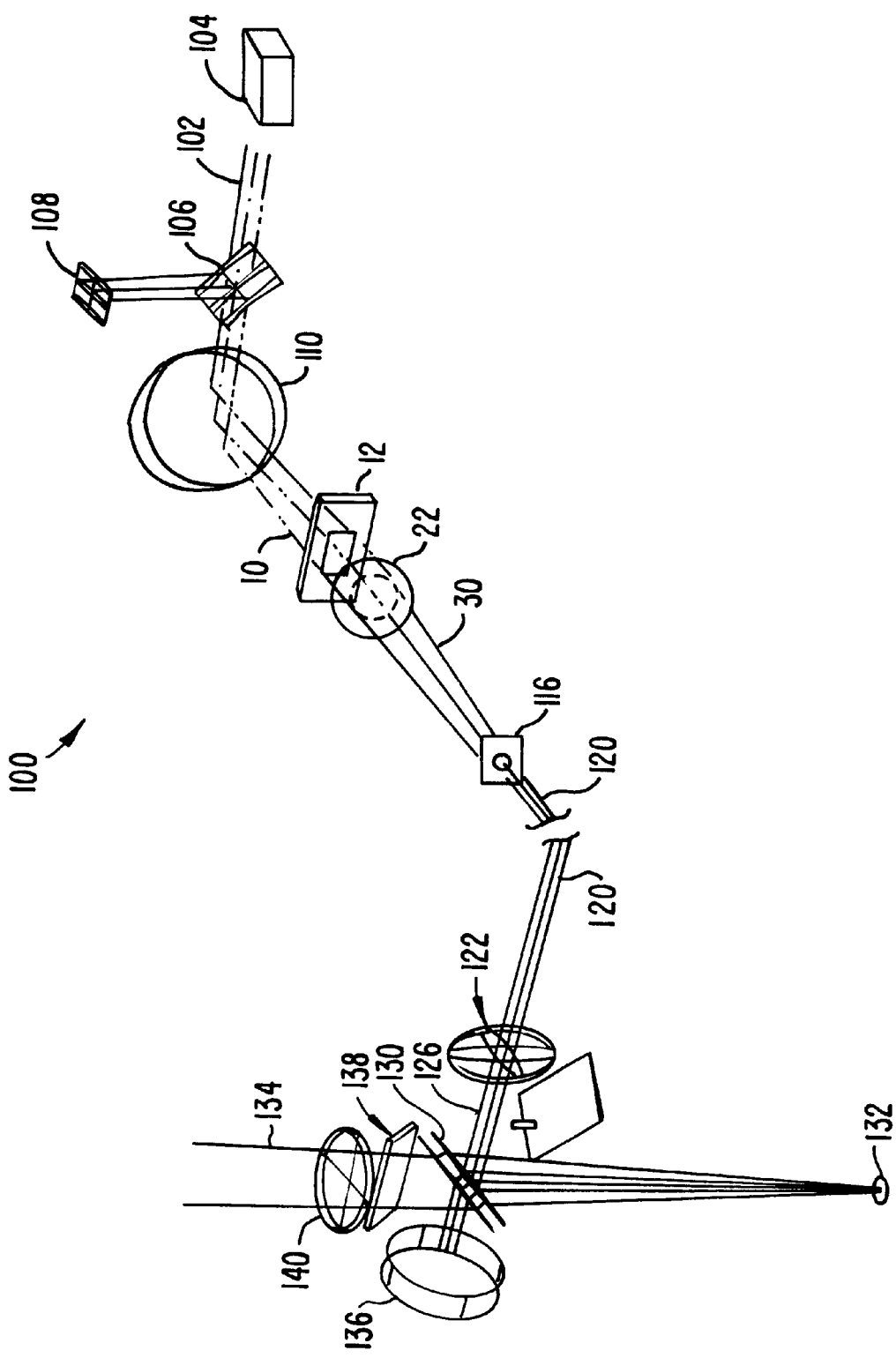
FIG. 8 is a schematic illustration of a beam scanning system employing the diffractive optics of the present invention.

FIG. 8 illustrates the incorporation of the invention in an ophthalmological laser surgery optical system 100 and the relative orientation of the components in the system 100. The particular components and configurations described below are merely for illustrative purposes. As discussed above, the diffractive optic apparatus can be used with a variety of different excimer laser systems.

As seen in FIG. 8, a beam 102 is generated from a suitable laser source 104, such as an argon fluoride (ArF) excimer laser beam source for generating a laser beam in the far ultraviolet range with a wavelength of about 193 nm. The wavelength typically ranges from about 192.5 to about 194 nm. The laser beam 102 is directed to a beam splitter 106. A portion of the beam 102 is reflected onto an energy detector 108, while the remaining portion is transmitted through the beam splitter 106 and reflected by a mirror 110 onto a rotating temporal beam integrator. An exemplary beam integrator is described in U.S. Pat. No. 5,646,791, although another type of temporal beam integrator may be used. The rotated beam emerging from the temporal integrator is directed to the diffractive optic apparatus 10 (FIG. 4). The beam 10 passes through the diffractive element 12 and beam expander assembly 22 and emerges as the annular beam 30. The annular beam 30 travels to the spatial integration plane 32 at which a variable aperture 116 is disposed. The spatial integration plane 32 is disposed near the focal point of the beam expander assembly 22. An apertured beam 120 emerges from the variable aperture 116. The variable aperture 116 is desirably a variable diameter iris combined with a variable width slit (not shown) used to tailor the size and profile of the beam 30 to a particular ophthalmological surgery procedure, such as photorefractive keratectomy (PRK) and phototherapeutic keratectomy (PTK). An exemplary variable iris and slit for use with this system is described in co-pending U.S. patent application Ser. No. 08/968,380, filed Nov. 12, 1997 (the full disclosure of which is incorporated herein by reference), which also describes a method and structure that could be used to offset the present beam geometries.

The apertured beam 120 is directed onto an imaging lens 122, which may be a biconvex singlet lens with a focal length of about 125 mm. The imaged beam 126 emerging from the imaging lens 122 is reflected by a mirror/beam splitter 130 onto the surgical plane 132. The apex of the cornea of the patient is typically positioned at the surgical plane 132. Imaging lens 122 may be moved transverse to the beam to offset the imaged beam in order to scan the imaged beam about the surgical plane 132. A treatment energy detector 136 senses the transmitted portion of the beam energy at the mirror/beam splitter 130. A beam splitter 138 and a microscope objective lens 140 form part of the observation optics. If desired, a beam splitter may be installed in the optical path of the beam 134 emanating from the microscope objective lens. The beam splitter is optically coupled to a video camera to assist in viewing or recording the surgical procedure. Similarly, a heads-up display may also be inserted in the optical path of the microscope objective lens 140 to provide an additional observational capability. Other ancillary components of the laser optical system 100 which are not necessary to an understanding of the invention such as the movable mechanical components driven by an astigmatism motor and an astigmatism angle motor, have been omitted to avoid prolixity.

The diffractive optic apparatus may be used for different laser systems, including scanning laser and large area laser ablation systems. An example is the VISX STAR Excimer Laser System™, which is commercially available from VISX, Incorporated of Santa Clara, Calif. This system produces an output of 193.0 nm, operates at a frequency of 6.0 Hz, and is adjusted to deliver uniform fluence of 160.0 mJ/cm$^2$ with a 6.0 mm diameter ablation zone. Other laser systems include the T-PRK® scanning and tracking laser from Autonomous Technologies Corporation, the SVS Apex laser from Summit Technology Inc., the Keracor™ 117 scanning laser system from Chiron Vision, and the like.

Figure 9:
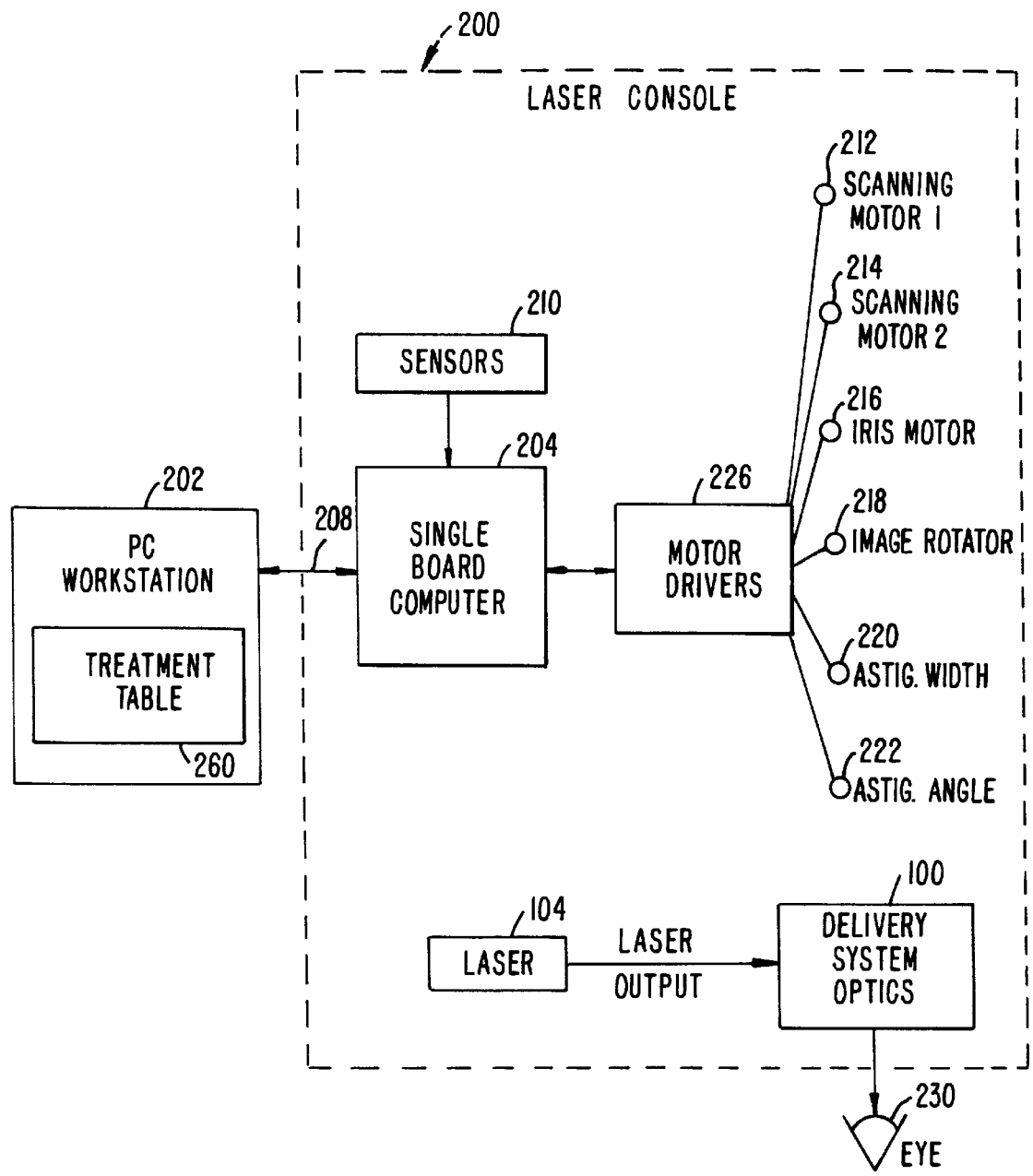
FIG. 9 is a block diagram illustrating a control system for the methods and systems of the present invention.

The block diagram of FIG. 9 illustrates an ophthalmological surgery control and treatment system 200 incorporating the invention that includes a personal computer (PC) work station 202 coupled to a single board computer 204 of the laser surgery system 200 by means of a first bus connection 208. The PC work station 202 and the subcomponents of the laser surgery unit 200 are known components and may comprise the elements of the VISX TWENTY/TWENTY EXCIMER LASER SYSTEM or the VISX STAR Excimer Laser Systems™, which are available from VISX, Incorporated, of Santa Clara, Calif. The laser surgery system 200 includes a plurality of sensors generally designated with reference numeral 210 which produce feedback signals from the movable mechanical and optical components in the ophthalmological laser surgery optical system 100 of FIG. 3 or FIG. 4. The movable mechanical and optical components include, for example, the elements driven by an iris motor 216, an image rotator 218, and astigmatism width motor 220, and an astigmatism angle motor 222. For scanning treatments where an ablation from an individual laser pulse is variably offset from the treatment center, optional scanning motor 1 (212) and scanning motor 2 (214) are provided. The moving lens 122 transverse to the beam 120 will provide this variable offset. The feedback signals from the sensors 210 are provided via appropriate signal conductors to the single board computer 204, which is desirably an STD bus compatible single board computer using a type 8031 microprocessor. The single board computer 204 controls the operation of the motor drivers generally designated with reference numerals 226 for operating the elements 216, 218, 220, and 222. In addition, the single board computer 204 controls the operation of the excimer laser 104, which is desirably an ArF laser with a 193 nm wavelength output designed to provide feedback stabilized fluence of 160 mJ/cm$^2$ at the cornea of the patient's eye 230 via the delivery system optics 100 of FIG. 3 or FIG. 4. Other ancillary components of the laser surgery system 200 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components, such as flexible and hard disk drives, memory boards and the like, have been omitted from the depiction of the PC work station 202.

The laser surgery system 200 may be used for procedures such as photorefractive keratectomy (PRK) and phototherapeutic keratectomy (PTK). Using PC workstation 202, an operator enters at least one patient treatment parameter such as the desired change in patient refraction. The above treatment parameter corresponds to an improved change corneal shape. The PC workstation 202 may then calculate treatment table 260 containing the positions of the laser elements during laser treatment. In addition to determining the sizes and geometries of successive treatment patterns, other laser elements which may be varied during treatment include variable aperture 116 and the position of the lens 112. In PRK, for instance, the laser surgery system 200 is used to ablate the tissue of the cornea after removal of the epithelium. The system may also be used for initial removal of the epithelium. To correct for myopia, successive annular laser beams 30 are projected on the cornea. The total ablation zone is typically a 0.5–6 mm circle. The correction for myopia reduces the radius of curvature of the cornea. This requires removal of more tissue in the center of the cornea and less tissue toward the peripheral treatment area. The annular geometry of the successive ablative beams is ideal for such treatment as the outer treatment segments can be exposed at lower dosages while the inner segments can be exposed at higher dosages to achieve the necessary treatment profile. This removes more tissue from the central region and brings the cornea to the desired contour having a decreased curvature. After the photorefractive keratectomy procedure, the epithelium rapidly regrows over the shaped area, producing a new anterior surface of the cornea. Alternatively, the epithelium is not removed but is partially severed and moved to the side for surgery and returned to its original position after the PRK.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An improved method for ablating corneal or epithelial tissue, said method being of the type wherein an ablative light beam is scanned over a corneal surface, said improvement comprising:

transforming the ablative light beam with a diffractive optical element to produce an annular geometry, the ablative light beam having a rectangular geometry before the diffractive optical element, wherein the diffractive optical element transforms the rectangular geometry to the annular geometry; and scanning the ablative light beam in the annular geometry to treat an entire ablation zone in the corneal tissue.

2. A method as in claim 1, wherein the scanning step comprises exposing the corneal tissue to a plurality of annular ablative light patterns, each for a predetermined time, wherein the patterns together cover the ablation zone.

3. A method as in claim 2, wherein the patterns do not substantially overlap.

4. An improved method for ablating corneal or epithelial tissue, said method being of the type wherein an ablative light beam is scanned over a corneal surface, said improvement comprising producing successive patterns of the ablative light beam by transforming the ablative light beam with a diffractive optical element to produce each of said patterns, the transforming of the ablative light beam including changing a Gaussian intensity distribution across the ablative light beam to a uniform intensity distribution across the patterns with the diffractive optical element, wherein said patterns have geometries selected to span an entire ablation zone in the corneal tissue without substantial overlap among said patterns, and wherein said scanning is performed so that the scanned patterns do not overlap.

5. A method as in claim 4, wherein said patterns are selected from the group consisting of annular rings, pie-shaped sections, and irregular sections.

6. A method as in claim 4, wherein a different diffractive optical element is used to produce each of said patterns.

7. A method as in claim 4, wherein the same diffractive optical element is used to produce at least two of said patterns.

8. An improved method for ablating corneal or epithelial tissue, said method being of the type wherein an ablative light beam is scanned over a corneal surface, said improvement comprising:

diffractively transforming the beam by passing the beam through a first diffractive optical element to produce a first ablative light pattern; and passing the beam through at least a second diffractive optical element different than the first diffractive optical element to produce a series of successive different patterns to treat an ablation zone in the corneal tissue.

9. A method as in claim 8, further comprising expanding the beam to provide successive patterns having different sizes.

10. A method as in claims 8 or 9 and, wherein the patterns have an annular geometry and the successive patterns differ only in size.

11. A method as in claim 8, wherein the diffractive optical elements change an energy intensity distribution of the ablative light beam to desired energy intensity distributions.

12. A method as in any of claims 1 to 9, wherein the ablative light energy is laser energy.

13. A method as in claim 12, wherein the laser energy has a wavelength of 193 nm.

14. A method as in any of claims 1 to 9, wherein successive geometries each have an area in the range from 0.01 mm$^2$ to 50.0 mm$^2$ and a power level in the range from 0.016 mJ to 80.0 mJ.

15. A method as in any of claim 1 to 9, wherein at least 3 successive patterns are produced.

16. A programming card for use with a system for ablating corneal tissue with ablative optical energy, said programming card comprising:

a tangible medium which stores computer readable code, wherein said code sets forth a method in accordance with any of claims 1 to 9.

17. An improved method for ablating corneal or epithelial tissue, said method being of the type wherein an ablative light beam is scanned over a corneal surface, said improvement comprising:

transforming the ablative light beam with a diffractive optical element to produce an annular geometry, wherein the ablative light beam has a Gaussian intensity distribution across the beam before the diffractive optical element, and wherein the diffractive optical element transforms the Gaussian beam intensity to an annular intensity distribution; and scanning the ablative light beam in the annular geometry to treat an entire ablation zone in the corneal tissue.

18. A method as in claim 17, wherein the transforming step is performed so that the annular intensity distribution comprises a uniform intensity.

19. A method as in claim 17, wherein the transforming step is performed so that the annular intensity distribution increases smoothly from an inner intensity along an inner perimeter of the annular geometry, and from an outer intensity along an outer perimeter of the annular geometry, to a maximum intensity therebetween.

* * * * *